United States Patent
Iga et al.

[11] Patent Number: 5,837,281
[45] Date of Patent: Nov. 17, 1998

[54] STABILIZED INTERFACE FOR IONTOPHORESIS

[75] Inventors: Katsumi Iga, Suita; Masafumi Misaki, Takarazuka; Keiichiro Okabe, Komae; Emi Kyo, Kawasaki, all of Japan

[73] Assignees: Takeda Chemical Industries, Ltd., Osaka; Advance Co., Ltd.; Teikoku Hormone Mfg. Co., Ltd., both of Tokyo, all of Japan

[21] Appl. No.: 614,375

[22] Filed: Mar. 12, 1996

[30] Foreign Application Priority Data

Mar. 17, 1995 [JP] Japan ........................... 7-086291

[51] Int. Cl.$^6$ ................ A61K 9/70; A61M 37/00; B32B 3/00
[52] U.S. Cl. ................ 424/449; 424/484; 428/245; 428/260; 428/262; 428/289; 428/304.4; 604/304; 604/305
[58] Field of Search ................ 424/486, 484, 424/488, 487, 449; 428/245, 260, 262, 289, 304.4; 604/304, 309, 307

[56] References Cited

U.S. PATENT DOCUMENTS

| | | |
|---|---|---|
| H1160 | 4/1993 | Maulding et al. ............ 604/20 |
| 4,328,319 | 5/1982 | Osipow et al. . |
| 4,738,849 | 4/1988 | Sawyer . |
| 5,059,425 | 10/1991 | Tsilibary et al. . |
| 5,152,996 | 10/1992 | Corey et al. . |
| 5,298,015 | 3/1994 | Komatsuzaki et al. . |
| 5,344,702 | 9/1994 | Haubs et al. . |
| 5,407,685 | 4/1995 | Malchesky et al. . |
| 5,447,940 | 9/1995 | Harvey et al. . |
| 5,520,916 | 5/1996 | Dorigatti et al. . |

FOREIGN PATENT DOCUMENTS

| | | |
|---|---|---|
| 0 643 981 A1 | 3/1995 | European Pat. Off. . |
| 6-16535 | 1/1994 | Japan . |
| 91/08795 | 6/1991 | WIPO . |
| 92/04938 | 4/1992 | WIPO . |

OTHER PUBLICATIONS

Patent Abstracts of Japan, vol. 018, No. 222 (C–1193) of JP–A–06 016535.

*Primary Examiner*—Edward J. Webman
*Attorney, Agent, or Firm*—Wenderoth, Lind & Ponack, LLP

[57] ABSTRACT

An interface is formed by incorporating (1) a mixture comprising a water-soluble protein and a drug into a matrix, or preferably (2) a mixture comprising a water-soluble protein and a drug to a porous matrix coated with a cationic surfactant or other ionic surfactant. The coating amount of the ionic surfactant is about 0.1 to 50 μg, and the content of the water-soluble protein is about 0.1 to 1,500 μg, each per 1 cm$^2$ of the matrix. The water-soluble protein includes an albumin and the drug includes a physiologically active peptide or protein, for example. The use of the stabilized interface inhibits decrease of the drug retaining amount, and insures an effective transdermal drug delivery with a high repeatability and accuracy.

31 Claims, 3 Drawing Sheets

STABILIZED INTERFACE FOR IONTOPHORESIS

BACKGROUND OF THE INVENTION

1. Field of the Invention

This invention relates to an interface (a skin contactor or patch) which is useful for transdermal administration of a drug (transdermal drug delivery) utilizing iontophoresis.

2. Description of Related Art

Iontophoresis is a system for stimulating transdermal absorption (endermic absorption) with the use of an electricity. The principle of such iontophoresis basically resides in stimulating or enhancing transmittance of a drug molecule through a skin barrier caused by, in an electric field between an anode and a cathode produced by an electric current, moving force of a positively charged molecule from the anode to the cathode, and a moving force of a negatively charged molecule from the cathode to the anode [see Journal of Controlled Release, 18, 213–220 (1992); Advanced Drug Delivery Review, 9, 119 (1992); Pharmaceutical Research, 3, 318–326 (1986)].

Recent advances of synthetic technologies and genetic engineering insure pure and mass production of a naturally-occurring peptide or protein, or a peptide or protein derivative in which the amino acid composition of the naturally-occurring peptide or protein is changed, or a chemically-modified derivative thereof. Further, such peptides and proteins are expected to be applied as drugs or medicaments. On the other hand, a strict control of administration (dosage) is required for exhibiting of the maximum drug effect, in a specific disease, of these peptides or proteins each having a variety of physiological activities even in a small amount and for minimizing a side effect (adverse affection).

Further, a physiologically active peptide or protein is usually decomposed in a gastrointestinal tract (digestive tract) by a digestive fluid or juice and hydrolyzed by a hydrolase present in the digestive tract wall, and hence absorption efficiency of the peptide or protein can hardly be improved effectively. Therefore, for expecting a sufficient drug effect, such physiologically active peptide or protein is usually administered not orally but by an injection. Administration as an injectable preparation, however, causes a great pain to a patient and burdens him with a heavy load since such injectable preparation can not be administered by himself.

In the field of pharmaceutical preparation, the iontophoresis is intensively researched as a new drug delivery system. That is, use of the iontophoresis provides an administration of a drug by a patient-self, which has been formerly administered as an injectable preparation, and hence improves a compliance and enhances a quality of life (QOL) of the patient.

In an administration system using the iontophoresis having such advantages, use is generally made of an electrode for applying a voltage with the use of a direct electric power unit, a drug-support (an interface as a skin contact) which is conductible to the electrode and capable of contacting a skin, and a reference electrode. As the drug-support (drug-retainer), there have been reported organic supports (e.g. a support comprising a paper material, a woven fabric, a nonwoven fabric or other fabric material, fibrous material or other spongy or porous material, and having absorbable member layer for impregnating and retaining (holding) an ionic drug fluid) and inorganic supports (e.g. a support comprising a ceramics having a porous or capillary structure or other non-electrically conductive member, or others).

However, when a drug is supported on such drug-support by coating or impregnating, or as dried and used for the iontophoresis, transdermal absorption amount of the drug is not sufficient. Therefore, the bioavailability of the drug can hardly be enhanced. Such small transdermal bioavailability is probably caused by an adsorption of the drug such as a physiologically active peptide or protein to the drug-support and decomposition of the drug during the storage due to instability of the drug.

Japanese Patent Application Laid-open No. 16535/1994 (JP-A-6-16535) proposes an effective enhancement of the transdermal absorbability even with a small amount of a drug, by the use of an interface for iontophoresis (skin contact) as produced by coating a porous or capillary structure composed of a non-electrically conductive material with a macro molecular protein such as a bovine serum albumin, a human serum albumin and gelatin. Use of the above interface insures improvement of the transdermal absorbability and bioavailability of a drug.

It is hard, however, to improve a residual ratio of the drug and hence to effectively utilize the drug. It is probably due to adsorption of the drug to the structure as a base material of the interface and instabilization of the drug. In particular, when a physiologically active peptide or protein is supported on the structure, the effective drug amount is remarkably decreased, probably because the adsorption amount of the peptide or protein relative to the porous or capillary structure is increased, or the peptide or protein is decomposed. Accordingly, the amount of the drug, and hence the dose are largely changed or affected according to a storage period of the interface, and thus a drug administration (drug delivery) with a high accuracy can hardly be achieved.

SUMMARY OF THE INVENTION

It is, therefore, an object of the present invention to provide an interface (skin contact) for iontophoresis which enhances the stability of a drug (medicament) and insures effective retention (possessing) of the drug.

It is another object of the present invention to provide an interface for iontophoresis which inhibits decrease of a retention amount of a drug and provides effective transdermal administration of the drug with a high repeatability and high accuracy.

A further object of the present invention is to provide an interface for iontophoresis which insures retention of even a physiologically active peptide or protein with a high stability and provides improvement of the bioavailability of the physiologically active peptide or protein.

It is a yet another object of the present invention to provide a stabilizing method for a drug in an interface for iontophoresis.

A still further object of the present invention is to provide a method of producing an interface for iontophoresis having excellent characteristics as above.

It is another object of the present invention to provide an applicator provided with the above-mentioned interface.

The inventors of the present invention made intensive investigations to accomplish the above-mentioned objects, and found that coating of a base material having a porous or capillary structure made of a non-electrically conductive material with an ionic surfactant and allowance of the coated base material to retain or passes a water-soluble protein and a drug in coexistence result in a remarkable enhancement of a stability of the drug and significant improvement of a bioavailability of the drug. The present invention has been accomplished based on the above findings and further investigations.

Thus, the interface for iontophoresis of the present invention comprises a matrix holding a mixture comprising a water-soluble protein and a drug. The matrix may be coated with an ionic surfactant, and the mixture comprising the water-soluble protein and the drug may be a homogeneous mixture. The ionic surfactant may for example be a cationic surfactant and the coating amount of the ionic surfactant may be about 0.1 to 50 μg per cm$^2$. The content of the water-soluble protein in the matrix may for instance, per cm$^2$, about 0.1 to 1,500 μg. The water-soluble protein includes, for example, a serum albumin or gelatin and others.

In the above interface, the stability of the drug is improved. The interface may be produced by, for example, (1) allowing a matrix to hold or support a mixture comprising a water-soluble protein and a drug, or preferably (2) coating a matrix with an ionic surfactant, and allowing the coated matrix to hold or support a mixture comprising a water-soluble protein and a drug. The applicator of the present invention is provided with an electrode applicable with a direct voltage, and the interface conductible to the electrode, capable of contacting a skin and feedable with a liquid for dissolution of a drug.

DETAILED DESCRIPTION OF THE INVENTION

Figure 1:
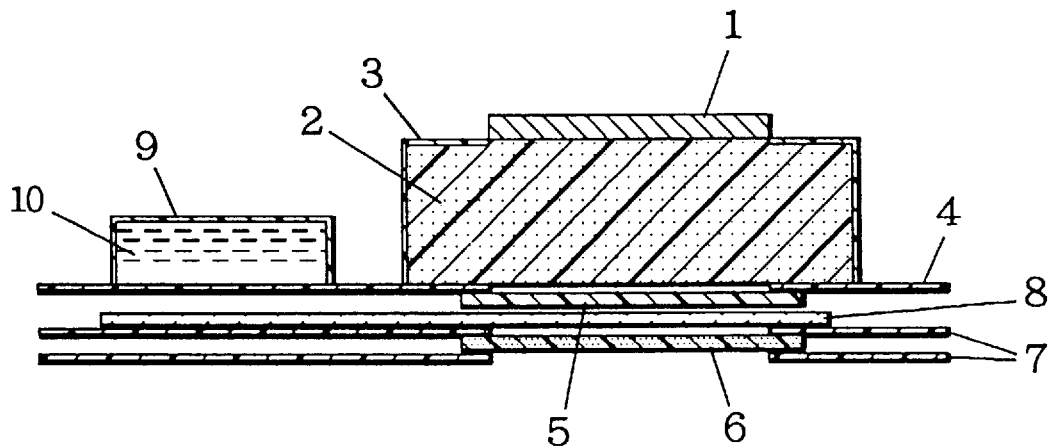
FIG. 1 is a cross sectional view illustrating an embodiment of an applicator.

The present invention is now described in detail with referring to the drawings where necessary.

As the matrix constituting the interface for iontophoresis (iontophoresis interface), use may be made of various members each having a porous or capillary structure which can retain or support a drug and through which the drug can be permeated (hereinafter briefly referred to as "porous body", "porous matrix" or "drug-support"). The porous body includes, for instance, organic porous bodies (e.g. fibrous aggregates made of cellulose and other naturally-occurring fibers, cellulose acetate and other semi-synthetic fibers, polyethylene, polypropylene, nylon, polyester and other synthetic fibers or mineral fibers, papers and other sheets, woven fabrics, nonwoven fabrics and other fabrics, a porous polypropylene, a porous polystyrene, a porous poly(methyl methacrylate), a porous nylon and other porous synthetic resins) and inorganic porous bodies (for instance, a biscuit (unglazed pottery), alumina, zirconia and other porous ceramics). Preferred porous matrix includes organic porous bodies such as nonwoven fabrics and porous synthetic resins, and porous ceramics.

The configuration of the porous body is not particularly restricted, and the porous body may practically be in the form of a sheet. The thickness of the sheet-like porous body can liberally be selected according to the retaining (holding) amount of the drug, and is for example about 0.01 to 1 mm, and preferably about 0.05 to 0.5 mm. The porous body may be undeformable body, but practically it may have flexibility. Further, the porous body may preferably be electrically nonconductive which does not conduct electricity.

The surface area of the sheet-like porous body may suitably be selected depending on the holding (retention capacity) amount of the drug, and is for instance about 1 to 10 cm$^2$, and preferably about 2 to 8 cm$^2$.

The pore size of the porous matrix may only be a size which provides retention capacity for a drug and insures permeation of the drug by means of iontophoresis, and the mean pore size may liberally be selected in the range of about 0.1 to 10 μm, and preferably about 0.2 to 5 μm.

The above-mentioned matrix is preferably coated with an ionic surfactant. It should be understood that the term "ionic surfactant" means a surfactant (surface active agent) having a hydrophilic group which dissociates in water and becomes ionic, and includes anionic surfactants, cationic surfactants and amphoteric surfactants. As examples of the anionic surfactant, there may be mentioned metallic soaps of fatty acids, alkyl sulfates (e.g. a sodium salt), alkylbenzene sulfonates (e.g. a sodium salt), alkyl naphthalene-sulfonates, α-olefin sulfonates (for instance a sodium salt), N-acyl amino acid salts (e.g. a sodium salt) and dialkyl 2-sulfosuccinates (for example a sodium salt). These anionic surfactants may be used singly or in combination.

The cationic surfactant includes, for instance, N-ethylalkaneamideammonium halides, alkylpyridinium halides (e.g. an N-C$_{10-20}$ alkylpyridinium bromide), quaternary ammonium salts and so forth. The quaternary ammonium salt includes, for example, alkyltrimethylammonium halides (e.g. a C$_{8-20}$ alkyl- trimethylammonium halide), dialkyldimethylammonium halides (e.g. a di-C$_{8-20}$ alkyldimethylammonium halide), alkylbenzyldimethylammonium halides shown by the following formula

wherein R represents an alkyl group and X represents a halogen atom [e.g. a C$_{8-20}$ alkylbenzyldimethylammonium chloride (benzalkonium chloride), a 4-C$_{1-10}$ alkylphenyloxyethoxyethylbenzyldimethylammonium chloride (e.g. benzethonium chloride)] and so forth. Such cationic surfactants can also be employed independently or in combination.

Examples of the amphoteric surfactant include an alkyl betaine, an alkyl diethylenetriaminoacetate and the like.

Among these ionic surfactants, surfactants each having a high safety and administered as a food additive or pharmaceutical additive are desirable. Preferred example of the ionic surfactant include cationic surfactants, in particular quaternary ammonium salts. The alkylbenzyldimethylammonium halide shown by the above formula (e.g. benzalkonium chloride, benzethonium chloride, etc.) can advantageously be employed among others.

The coating amount of the ionic surfactant relative to the matrix may be selected from a range as far as the stability of the drug can be improved, and, for example, about 0.10 to 50 μg, preferably about 0.10 to 30 μg and more preferably about 0.12 to 12 μg of the ionic surfactants is coated per 1 cm$^2$ of the matrix.

The relative coating amount of the ionic surfactant to the porous matrix may practically be about 0.001 to 10% by weight, preferably about 0.005 to 5% by weight, and more preferably about 0.01 to 1% by weight. The porous matrix is practically coated with about 0.005 to 1% by weight of the ionic surfactant.

The matrix coated with the ionic surfactant contains a mixture of a water-soluble protein and a drug. The term "water-soluble protein" as used in this specification means a protein having a solubility of 5 g or more, preferably 10 g or more, relative to 100 ml of water at about 20° C., and this "water-soluble protein" used in this specification does not include within its meanings the above mentioned drug. The embodiment of the mixture of the water-soluble protein and the drug held in the matrix is not particularly restricted, and the mixture may be retained or supported on the matrix by, for example, dropping, spraying or other technique.

The water-soluble protein includes, for example, animal proteins including water-soluble simple proteins, conjugated proteins, derived proteins except for the below-mentioned drug. Examples of the water-soluble protein include an albumin (e.g. a bovine serum albumin (BSA), a human serum albumin (HSA) and other serum albumins, ovalbumin, milk albumin, globin and the like), gelatin, proteins which are treated with an alkali, acylation or other chemical modification to improve the solubility in water, and enzymatically-modified proteis such as those modified with a protease, a phosphoprotein-phosphatase or the like. Preferred water-soluble protein includes a bovine serum albumin (BSA), a human serum albumin (HSA) and other serum albumins and gelatin. These water-soluble proteins may be used singly or in association.

The proportion of the water-soluble protein may be selected from a range not interfering with the stability of the drug, and is for instance about 0.1 to 1,500 μg, and preferably about 0.4 to 1,200 μg relative to 1 cm$^2$ of the matrix.

The retaining amount (supporting amount) of the water-soluble protein is about 0.01 to 30% by weight, preferably about 0.05 to 10% by weight, and more preferably about 0.1 to 5% by weight relative to the porous matrix, for instance. The matrix may practically retain or support the water-soluble protein in a proportion of about 0.1 to 10% by weight relative to the matrix.

The drug includes a variety of drugs (medicaments) which are transdermally or endermically absorbable, such as physiologically active peptides or proteins each having a molecular weight of about 10,000 or less (e.g. about 100 to 10,000, preferably about 200 to 8,000), and drugs (physiologically active compounds) each having a low molecular weight.

As the physiologically active peptide, there may be mentioned for example the following peptides:

Luteinizing hormone-releasing hormone (LH-RH), derivatives each having a similar function to LH-RH, such as a polypeptide shown by the following formula (I):

(Pyr) Glu-R$^1$-Trp-Ser-R$^2$-R$^3$-R$^4$-Arg-Pro-R$^5$     (I)

wherein R$^1$ represents His, Tyr, Trp or p-NH$_2$-Phe, R$^2$ represents Tyr or Phe, R$^3$ indicates Gly or a D-amino acid residue, R$^4$ denotes Leu, Ile or Nle, R$^5$ represents Gly-NH-R$^6$, where R$^6$ denotes a hydrogen atom or a lower alkyl group which may have a hydroxyl group, or NH-R$^6$, where R$^6$ has the same meaning as above, or a salt thereof [see U.S. Pat. No. 3,853,837, U.S. Pat. No. 4,008,209, U.S. Pat. No. 3,972,859, British Patent No. 1423083, Proceedings of the National Academy of Science, 87, 6509–6512 (1981)].

LH-RH antagonists such as a polypeptide shown by the following formula (II):

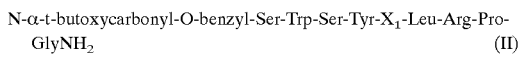

N-α-t-butoxycarbonyl-O-benzyl-Ser-Trp-Ser-Tyr-X$_1$-Leu-Arg-Pro-GlyNH$_2$     (II)

wherein X$_1$ represents D-Ser or D-Trp, or a salt thereof [see U.S. Pat. Nos. 4,086,219, 4,124,577, 4,253,997, and 4,317,815].

Insulin; somatostatin, somatostatin derivatives, such as a polypeptide shown by the following formula (III):

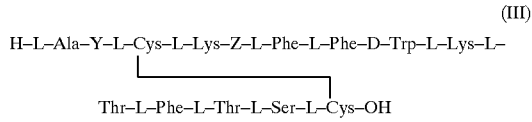

(III)
H-L-Ala-Y-L-Cys-L-Lys-Z-L-Phe-L-Phe-D-Trp-L-Lys-L-
Thr-L-Phe-L-Thr-L-Ser-L-Cys-OH wherein Y represents D-Ala, D-Ser or D-Val, Z represents Asn or Ala, or a salt thereof [see U.S. Pat. Nos. 4,087,390, 4,093,574, 4,100,117 and 4,253,998].

Adrenocorticotropic hormone (ACTH); melanocyte-stimulating hormone (MSH); thyroid-stimulating hormone (TSH), thyroid-stimulating hormone-releasing hormone (TRH), their derivatives, such as a compound shown by the following formula (IV):

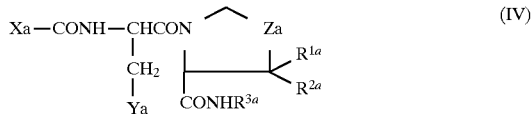

wherein X$^a$ represents a 4- to 6-membered heterocyclic group, Y$^a$ denotes imidazol-4-yl or 4-hydroxylphenyl group, Z$^a$ represents CH$_2$ or S, R$^{1a}$ and R$^{2a}$ independently represent a hydrogen atom or a lower alkyl group, and R$^{3a}$ represents a hydrogen atom or an optionally substituted aralkyl group, or a salt thereof [see Japanese Patent Application Laid-open No. 121273/1975 (JP-A-50-121273), Japanese Patent Application Laid-open No. 116465/1977 (JP-A-52-116465)]; vasopressin, vasopressin derivatives {desmopressin [see Journal of Society of Endocrinology, Japan, 54, No.5, 676–691 (1978)]}.

Oxytocin; calcitonin, derivatives each having a similar function as calcitonin, such as a compound shown by the following formula (VI):

(VI)
Cys — Ser — Asn — Leu — Ser — Thr — X$^b$ — Val — Leu — Gly — Lys — Leu — Ser — Gln — Glu — Leu — His —
Lys — Leu — Gln — Thr — Tyr — Pro — Arg — Thr — Asp — Val — Gly — Ala — Gly — Thr — Pro wherein X$^b$ represents 2-aminosberic acid, or a salt thereof [Endocrinology, 1992, 131/6 (2885–2890)].

Glucagon; gastrins; secretin; cholecystokinin; angiotensin; enkephalin, enkephalin derivatives, such as a peptide shown by the following formula (VII):

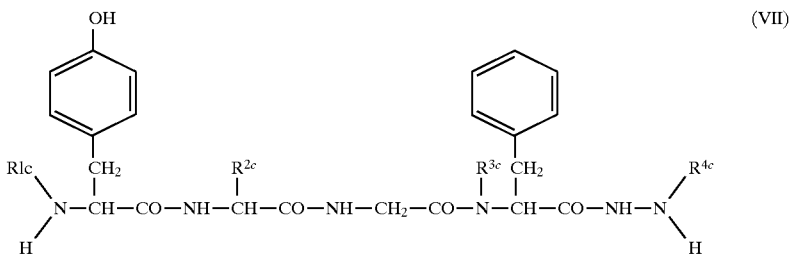

(VII)

wherein $R^{1c}$ and $R^{3c}$ respectively represent a hydrogen atom or an alkyl group having 1 to 6 carbon atoms, $R^{2c}$ represents a hydrogen atom or a D-α-amino acid, $R^{4c}$ denotes a hydrogen atom or an optionally substituted aliphatic acyl group having 1 to 8 carbon atoms, or a salt thereof (see U.S. Pat. No. 4,277,394, European Patent Application Laid-open No. 31567) and other oligopeptides and endorphins.

Kyotorphine; interleukins (I to XI); tuftsin; thymopoietin; thymus humoral factor (THF); factor of thymus in serum (FTS) and their derivatives such as a peptide shown by the following formula (VIII):

PGlu-$X^d$-Lys-Ser-Gln-$Y^d$-$Z^d$-Ser-Asn-OH (VIII)

wherein $X^d$ represents L- or D-Ala, $Y^d$ and $Z^d$ independently represent Gly or a D-amino acid having 3 to 9 carbon atoms, or a salt thereof (see U.S. Pat. No. 4,229,438); and other thymus hormones [e.g. thymocin $α_1$ and $β_4$, thymic factor X, etc. "Journal of Clinical Experimental Medicine (IGAKU NO AYUMI)" 125, No. 10, 835–843 (1983)].

Motilin; dynorphin; bombesin; neurotensin; cerulein; bradykinin; urokinase; substance P; polymyxin B; colistin; gramicidin; bacitracin; protein synthesis-stimulating peptide (British Patent No. 8232082); gastric inhibitory polypeptide (GIP); vasoactive intestinal polypeptide (VIP); platelet-derived growth factor (PDGF); growth hormone-releasing factor (GRF, somatoclinine, etc.) and growth hormone-releasing peptide.

These physiologically active peptides may be human peptides, or peptides derived from other animals such as a bovine, a swine, a chicken, a salmon, an eel and so on. By way of example, insulin may be a swine-derived insulin. Further, a chimera of a human insulin and an insulin derived from the above-mentioned animal, or an active derivative in which a part of the structure of the peptide has been changed.

The drug having a low molecular weight includes compounds each having a molecular weight of about 1,000 or less (e.g. about 100 to 1,000, preferably about 200 to 800) and having a pharmacological activity. The species of the drug having a low molecular weight is not critical, and it may be whichever of a central nervous system drug, an antiallergic agent, a circulatory drug, a respiratory drug, a drug for digestive system, a hormone, a metabolic drug, an antitumor drug (antineoplastic drug), an antibiotic, a chemotherapeutic drug or others. In more detail, as examples of the drug having a low molecular weight, there may be mentioned antibiotics, antimycosis (antifungal drugs), hypolipidermic drugs, circulatory drugs, antiplatelet drugs, antitumors, antipyretic, analgesic and/or antiinflammatory agents, antitussive-expectorant agents, sedatives, muscle relaxants, antiepileptic drugs, antiulcer drugs, antidepressant agents, antiallergic agents, cardiotonics, antiarrhythmic agents, vasodilators, hypotensive-diuretic agents, drugs for diabetes, anticoagulants, hemostatic agents, antituberculosis drugs, hormones, narcotic antagonists, bone resorption-inhibitory agents, vascularization-inhibitory drugs and so forth.

As examples of the antibiotic, there may be mentioned gentamycin, dibekacin, kanendomycin (bekanamycin sulfate), lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin (cephalothin), cefaloridine (cephaloridine), cefotiam, cefsulodin, cefmenoxime, cefmetazole, cefazolin, cefotaxime, cefoperazon, ceftizoxime, moxalactam, tienamycin, sulfazecin, aztreonam and so on.

The antifungal agent include, for instance, 2-[(1R,2R)-2-(2,4-difluorophenyl-2-hydroxy-1-methyl-3-(1H-1,2,4-triazol-1-yl)propyl]-4-[4-(2,2,3,3-tetrafluoropropoxy) phenyl]-3(2H,4H)-1,2,4-triazolone and the like.

Examples of the hypolipidermic drug (antihyperlipidermic drug) include pravastatin and simvastatin. The circulatory drug includes delapril hydrochloride, for instance.

As the antiplatelet drug, there may be mentioned, for example, ticlopidine, cilostazol, alprostadil, limaprostat, dipyridamole, ethyl icosapentate, beraprost, ozagrel, aspirin and the like.

The antitumor drug (antineoplastic agent) include, for instance, bleomycin hydrochloride, methotrexate, actinomycin-D, mitomycin-C, vinblastine sulfate, vincristine sulfate, daunorubicin hydrochloride, adriamycin, neocarzinostatin, cytosine arabinoside, fluorouracil, tetrahydrofuryl-5-fluorouracil, krestin, picibanil, lentinan, levamisole, bestatin (ubenimex), azimexon, glycyrrhizin, poly I:C, poly A:U, poly ICLC and so forth.

As examples of the antipyretic, analgesic and/or antiinflammatory agent, there may be mentioned sodium salicylate, sulpyrine, sodium flufenamate, diclofenac sodium, indomethacin sodium, morphine hydrochloride, pethidine hydrochloride, levorphanol tartarate, oxymorphone and so on.

The antitussive/expectorant agent includes, for example, ephedrine hydrochloride, methylephedrine hydrochloride, noscapine hydrochloride, codeine phosphate, dihydrocodeine phosphate, alloclamide hydrochloride, clofedianol hydrochloride, picoperidomine hydrochloride, chloperastine, protokylol hydrochloride, isoproterenol hydrochloride, salbutamol sulfate, terbutaline sulfate.

As the sedative, there may be mentioned, for example, chlorpromazine hydrochloride, allochlorperazine, trifluoperazine, atropine sulfate, scopolamine methyl bromide, etc. Examples of the muscle relaxant include pridinol methanesulfonate, tubocurarine chloride and pancuronium bromide.

As the antiepileptic agent, there may be mentioned for instance phenytoin sodium, ethosuximide, acetazolamide sodium, chlordiazepoxide hydrochloride and so forth. The antiulcer drug include, for example, metoclopramide and histidine hydrochloride. The antidepressant includes, for instance, with imipramine, clomipramine, noxiptilin, phenelzine sulfate and so on.

Examples of the antiallergic drug include diphenhydramine hydrochloride, chlorpheniramine maleate, tripelennamine hydrochloride, methdilazine hydro-chloride, clemizole hydrochloride, diphenylpyraline hydrochloride, methoxyphenamine hydrochloride and so forth.

As the cardiotonic, there may be mentioned trans-Π-oxocamphor, theophyllol, aminophylline, etilefrine hydrochloride, for instance. The antiarrhythmic agent includes, for example, propranolol hydrochloride, alprenolol hydrochloride, bufetolol hydrochloride, oxprenolol hydrochloride and the like.

As examples of the vasodilator, there may be mentioned oxyfedrine hydrochloride, diltiazem hydrochloride, tolazoline hydrochloride, hexobendine and bamethan sulfate. The hypotensive-diuretic agent includes, for instance, hexamethonium bromide, pentolinium, mecamylamine hydrochloride, ecarazine hydrochloride, clonidine hydrochloride and so on.

Examples of the antidiabetic agent (hypoglycemic drug) include glymidine sodium, glipizide, phenformin hydrochloride, buformin hydrochloride, metformin and the like. The anticoagulant includes, for instance, heparin sodium and sodium citrate. The hemastatic includes thromboplastin, thrombin, meradione sodium bisulfite, acetomenaphtone, ε-aminocaproic acid, tranexamic acid, carbazochrome sodium sulfate, adrenochrome monoamino guanidine methanesulfonate, for example.

As the antituberculosis drug, there may be mentioned isoniazid, ethambutol and sodium p-amino-salicylate, for example.

Examples of the hormone include prednisolone succinate, prednisolone sodium phosphate, dexamethasone sodium sulfate, betamethasone sodium phosphate, hexestrol phosphate, hexestrol acetate and methimazole.

The narcotic antagonist includes, for example, levallorphan tartrate, nalorphine hydrochloride, naloxone hydrochloride and so forth. As examples of the bone resorption inhibitory drug, there may be mentioned (sulfur-containing alkyl) aminomethylene bisphosphoate.

As the vascularization inhibitory drug, there may be mentioned, for instance, a vascularization inhibitory steroid [see Science 221, 719 (1983)], fumagillin, (European Patent Application Laid-open No. 325119), fumagillol derivatives, [e.g. O-monochloroacetylcarbamoylfumagilol, O-dichloroacetylcarbamoylfumagillol (see European Patent Application Laid-open Nos. 357061, 359036, 386667 and 415294)].

Preferred drug includes, for example, physiologically active peptides and derivatives thereof, such as adrenocorticotropic hormone, insulin, secretin, oxytocin, angiotensin, β-endorphin, glucagon, vasopressin, somatostatin, gastrins, luteinizing hormone-releasing hormone, enkephalins, neurotensin, atrial natriuretic peptide, growth hormone, bradykinin, substance P, dynorphin, thyroid-stimulating hormone, prolactin, interferons, interleukins, G-CSF, glutathio-peroxidase, superoxide dismutase, desmopressin, somatomedin, endothelin, calcitonins, and salts of these peptides.

Typically preferred physiologically active peptide includes, a calcitonin, its derivative or its salt (hereinafter briefly referred to as "the calcitonin"). The calcitonin includes, for instance, calcitonins derived from mammals such as a human being, a swine and so on (e.g. a human calcitonin, a swine calcitonin), calcitonins derived from birds such as a chicken, calcitonins derived from fishes such as a salmon and an eel (e.g. a salmon calcitonin, an eel calcitonin) and calcitonins derived from other animals or plants (vegetables). Further, the calcitonin may be a chimera derived from a human calcitonin and a calcitonin of other animal, for example a chimera derived from a salmon calcitonin and a human calcitonin, a chimera derived from an eel calcitonin and a human calcitonin, or the like. Moreover, the calcitonin may be a calcitonin in which a part or the whole of the structure of the amino acids constituting the calcitonin or the structure of side chain is artificially changed.

Typical example of the calcitonin includes a peptide shown by the following formula (IX):

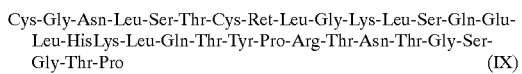

Cys-Gly-Asn-Leu-Ser-Thr-Cys-Ret-Leu-Gly-Lys-Leu-Ser-Gln-Glu-Leu-HisLys-Leu-Gln-Thr-Tyr-Pro-Arg-Thr-Asn-Thr-Gly-Ser-Gly-Thr-Pro (IX)

[Endocrinology 1992, 131/6 (2885–2890)].

Further, the derivative having a similar function to calcitonin includes, for instance, a compound of the formula (VI) or its salt.

Examples of the salt of calcitonin include salts with inorganic acids such as hydrochloric acid, sulfuric acid, hydrobromic acid and phosphoric acid; salts with organic acids such as formic acid, acetic acid, propionic acid, glycolic acid, oxalic acid, succinic acid, tartaric acid, citric acid, benzenesulfonic acid and p-toluenesulfonic acid; complex salts with inorganic compounds such as calcium and magnesium and so on.

The relative proportion of the drug to the porous matrix (drug-retainer) may only be an effective amount according to the species of the drug, an animal to be administered, the part to be administered or other factors. The retaining (possessing) amount of the drug is, for example, about 0.1 to 100 μg, and preferably about 0.5 to 50 μg relative to 1 cm$^2$ of the porous matrix.

The drug and the water-soluble protein may be retained or possessed throughout the whole of the porous matrix, but they may preferably be retained in coexistence in a part to. be contacted by a skin of a living body, of the porous matrix. Desirably, the water-soluble protein and the drug may be possessed in the matrix as a homogeneous mixture in the skin contactor.

The interface (skin contact) of the present invention may be prepared by, for instance, holding or supporting a homogeneous mixture of the water-soluble protein and the drug to the matrix (e.g. as a solution containing the water-soluble protein and the drug), by means of dropping, spray or others. The interface of the present invention may also be obtained by coating the matrix with the ionic surfactant by means of, for example, impregnating, spray coating or other technique, drying the coated matrix, and retaining or supporting a mixture of the water-soluble protein and the drug, by means of dropping, spraying or other technology. To the porous matrix coated with the ionic surfactant, the water-soluble protein and the drug may be retained or supported concurrently, or they may be retained or supported in a suitable order. By way of illustration, the drug may be retained or supported to the matrix after retention or supporting of the water-soluble protein. The water-soluble protein and the drug may be retained or supported to the porous matrix by dropping or spraying, and drying the resultant. Preferably, the water-soluble protein is retained or supported concurrently (together) with the drug to the porous matrix coated with the ionic surfactant.

The interface is useful for transdermal administration of a drug (transdermal drug delivery) by iontophoresis with the use of a various applicator applicable to a skin. FIG. 1 is a cross sectional view illustrating an embodiment of an applicator equipped with the above-mentioned interface.

The applicator illustrated in FIG. 1 is provided with a support (base member) 4 having a flexibility and being formed with an opening, and an electrode 1 such as a silver electrode. Further, the applicator is provided with a first container (reservoir) 3 and a second container (reservoir) 9, and the first container 3 accommodates an electrically conductive gel 2 such as a hydrated gel of NaCl-containing poly(vinyl alcohol) (PVA), and is disposed on the support 4 in the part corresponding to the opening, and the second container 9 reserves a liquid (fluid) 10 for dissolution of the drug such as a distilled water for injection (Fuso Chemical Industries, Ltd., Japan), and constitutes a reservoir disposed on the support 4.

The opening of the support 4 which is formed for insuring the movement of electric charges is provided with an ion exchange membrane 5, the inner surface of which faces to the electrically conductive gel 2 of the container 3, and the outer surface of the ion exchange membrane is laminated with an interface (porous body) 6 through a nonwoven fabric 8 disposed in the area from the opening of the support 4 (the part of the container 3) toward the part of the second container 9. To the interface 6 is attached an adhesive tape 7 for applying the applicator to a skin in a manner which leaves open an area of the interface corresponding to the opening of the support 4. The electrically conductive gel 2 of the first container 3 is conductible with the electrode 1 and contactible with the ion exchange membrane 5 through the opening. The size of the opening of the support 4 is not critically limited, but preferably the opening may be almost the same size with a skin contact surface of the interface 6.

The containers 3, 9 can be formed of, for instance, polyethylene or other synthetic resins. As the ion exchange membrane 5, use can be made of various membranes each having ion exchange capability, such as "AC220 Membrane" (trade name) manufactured by Asahi Chemical Industries, Japan. As the nonwoven fabric 8, use may be made of a variety of nonwoven fabrics through which a liquid is permeable, such as "Benberg Half" (trade name) manufactured by Asahi Chemical Industries, Japan. Further, various organic porous bodies or inorganic porous bodies such as porous membrane of a nylon porous body (trade name: "Biodyne Plus", Nihon Pall Ltd., Japan) and the like can be used as the porous matrix of the interface 6. As the adhesive tape 7, various adhesive tapes each having adhesive properties to a skin, such as "Blenderm" (trade name) manufactured by 3M Pharmaceuticals, M.N. (Minnesota) may be employed.

Such applicator may be pierced by, for example, inserting a needle through the second container 9 and the support 4 to form a pore in the support 4 connecting to the inside of the second container 9, so that the liquid 10 for dissolution of the drug is permeated to the nonwoven fabric 8 to reach (to be supplied or fed) to the interface 6 possessing the drug.

Incidentally, the second container is not always required, and a liquid for dissolving the drug may be injectable (feedable) to the interface retaining the drug. In such an embodiment of an applicator, the nonwoven fabric is not necessarily required.

Figure 2:
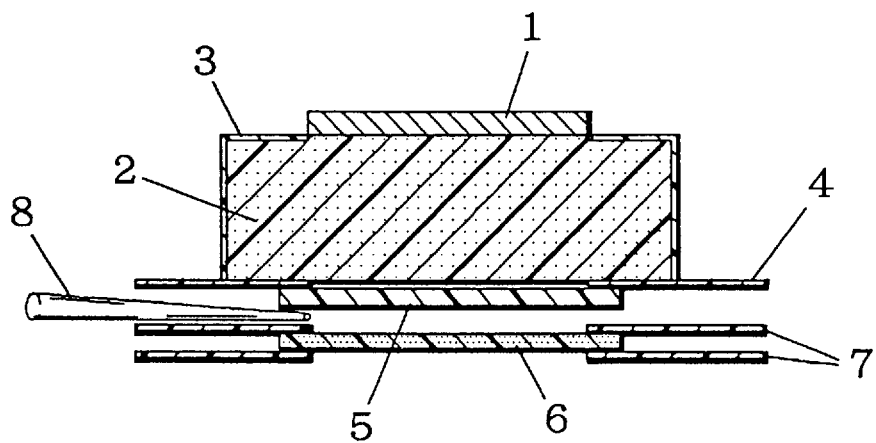
FIG. 2 is a cross sectional view showing another embodiment of the applicator.

FIG. 2 is a cross sectional view illustrating another embodiment of an applicator. This applicator is provided with a support, and a first container 3 having an electrode 1 and accommodating an electrically conductive gel 2 as the same with the applicator shown in FIG. 1. Further, an interface (porous body) 6 is laminated (piled up), through an ion exchange membrane 5, to the part corresponding to an opening of the support 4. Furthermore, an adhesive tape (pressure-sensitive tape) 7 is attached to the interface 6 in a manner which leaves open an area of the interface corresponding to the opening of the support 4, in the same manner as above. Between the ion exchange membrane 5 and the interface 6 is formed an injection port which is capable of injecting a liquid.

When such applicator is used, a nozzle tip of a injection tip 8 may be inserted to the injection port between the ion exchange membrane 5 and the interface 6 to inject a liquid for dissolving the drug such as a distilled water for injection to the interface 6 which possess the drug. The injecting amount of the liquid may be selected from a range as far as the drug can be dissolved according to the size of the applicator, the surface area of the interface, the retaining amount of the drug, and usually is about 30 to 500 $\mu$l and preferably about 50 to 200 $\mu$l.

It is effective to incorporate an adsorption accelerator (e.g. monoterpenes, fatty acid monoglycerides, etc.) into the liquid for dissolving the drug for accelerating the absorption of the drug.

The transdermal delivery (administration) of the drug by means of iontophoresis can be effected by applying a direct-current voltage to the electrode of the applicator and a reference electrode to pass an electricity. As the direct-current voltage, not only a continuous direct current voltage but also a direct current pulse voltage can be utilized. The applied voltage may be selected from a range not injuring the skin of a living body and not adversely affecting the transdermal absorption ratio, and is, for example, about 1 to 20 V, and preferably about 3 to 15 V. By allowing the surface to be contacted to a skin (skin contact surface) of the interface and the reference electrode to contact with the skin, and applying a voltage, a circuit can be formed as the skin being as an electric conductor so that the electric application can be effected.

Incidentally, materials of the electrode and the reference electrode are not particularly limited, and include silver and other metals, electric-conductible rubbers, electric conductible polymers, carbon films, metal foils such as aluminum foils. The size and the shape (configuration) of the electrode and the reference electrode may be the same or different. Further, the interface of the invention can be applied to not only human beings but also other mammals such as dogs, cats, hoses, cows, rabbits and swine.

The interface of the present invention, which comprises a matrix, preferably coated with an ionic surfactant, and a water-soluble protein and a drug possessed by the matrix, insures enhancement of the stability of the drug and provides effective retention of the drug. Further, since the interface can suppress or inhibit the decrease of the retention amount of the drug, it insures effective transdermal administration of the drug with a high repeatability and a high accuracy. Furthermore, it provides retention of even a physiologically active peptide or protein with a high stability, and hence improves the bioavailability of the physiologically active peptide or protein. Accordingly, by using the interface, the drug can be absorbed transdermally with a high efficiency and hence strict control of the dose can be achieved.

The following examples are intended to illustrate the present invention in more detail, but should by no means limit the scope of the invention.

EXAMPLES

Example 1

To a porous matrix (Biodyne Plus Membrane, Nihon Pall Ltd., Japan, 2.5 cm$^2$) was impregnated 0.01% by weight of an ionic surfactant (benzalkonium chloride) and the impregnated matrix was dried. To the resultant porous matrix comprising the ionic surfactant was dropped 10 μl of an aqueous solution containing 1% by weight of a bovine serum albumin (BSA) and 20 International Units (4 μg) of a salmon calcitonin (a synthetic salmon calcitonin; Teikoku Hormone Mfg. Co., Ltd., Japan), and the resultant was dried to provide a calcitonin-possessing membrane (interface).

Comparative Example 1

To the porous matrix (Biodyne Plus Membrane, Nihon Pall Ltd., Japan; 2.5 cm$^2$) used in the Example 1, without being coated with an ionic surfactant, was added 10 μl of an aqueous solution containing 20 International Units (4 μg) of a salmon calcitonin (a synthetic salmon calcitonin; Teikoku Hormone Mfg. Co., Ltd., Japan), and the resultant was dried to provide a calcitonin-possessing membrane (interface).

Comparative Example 2

The porous matrix (Biodyne Plus Membrane, Nihon Pall Ltd., Japan; 2.5 cm$^2$) used in Example 1 was treated with an ionic surfactant in the same manner as Example 1. To the treated matrix was added 10 μl of an aqueous solution containing 20 International Units (4 μg) of a salmon calcitonin (a synthetic salmon calcitonin; Teikoku Hormone Mfg. Co., Ltd., Japan) and the resultant was dried to give a calcitonin-possessing membrane (interface).

The calcitonin-retaining membranes each obtained in the above example and comparative examples were stored at 75% RH and at 5° C. for 4 weeks, and the stability of the calcitonin was investigated in the following manner.

That is, each calcitonin-retaining membrane was extracted with 5 mM sodium acetate buffer (pH 4) containing 0.1% of Tween 20 and 0.9% of sodium chloride, and 150 μl of 0.2 M phosphoric acid buffer (pH 9) and 200 μl of acetonitrile solution containing 0.3 mg/ml of fluorescamine were added to 450 μl of the calcitonin extract for fluorescent-labelling of the mixture with the use of fluorescamine. The resultant mixture (50 μl) was injected into a high performance liquid chromatography column, and thus the amount of the calcitonin remained in the retaining membrane was determined. The results are set forth in FIG. 3. The conditions for the high performance liquid chromatography are as follows:

Pump: Hitachi Intelligent Pump L-6200

Moving phase: 30 to 45% acetonitrile/10 mM phosphoric acid buffer (pH 8)

Flow rate: 0.8 ml/min.

Column: Octadecyl-2PW (Tosoh Co., Ltd., Japan)

Detector: Hitachi Fluorescent Detector F-1080, Ex; 390 nm, Em; 475 nm

Figure 3:
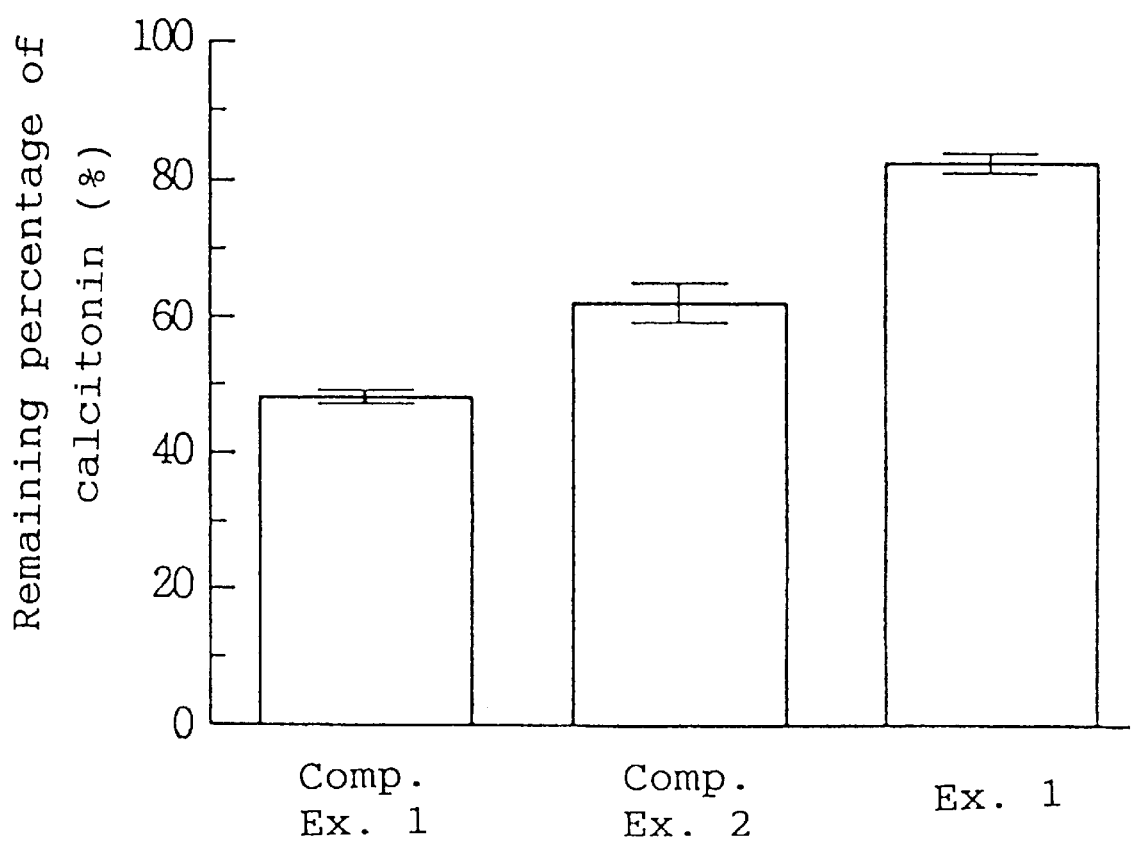
FIG. 3 is a graph illustrating the results in Example 1, Comparative Example 1 and Comparative Example 2.

As shown in FIG. 3, the remaining ratios of the calcitonin in the interfaces each obtained in Comparative Examples 1 and 2 were 48% and 62%, respectively. In contrast, the interface obtained by Example 1 showed a higher remaining ratio of calcitonin of 81%.

Example 2

Benzalkonium chloride (0.01% by weight) was incorporated into a porous matrix (Biodyne Plus Membrane) in the same manner as Example 1. To the treated matrix was dropped 10 μl of an aqueous solution containing 1% by weight of BSA and 100 International Units (20 μg) of a salmon calcitonin, and the resultant was dried to give an interface retaining the calcitonin (drug-retaining membrane). Further, by using the obtained interface, an applicator shown in FIG. 2 was manufactured.

Comparative Example 3

The procedure of Example 2 was repeated except that BSA was not used to provide an interface (drug-holding membrane) and an applicator.

Figure 4:
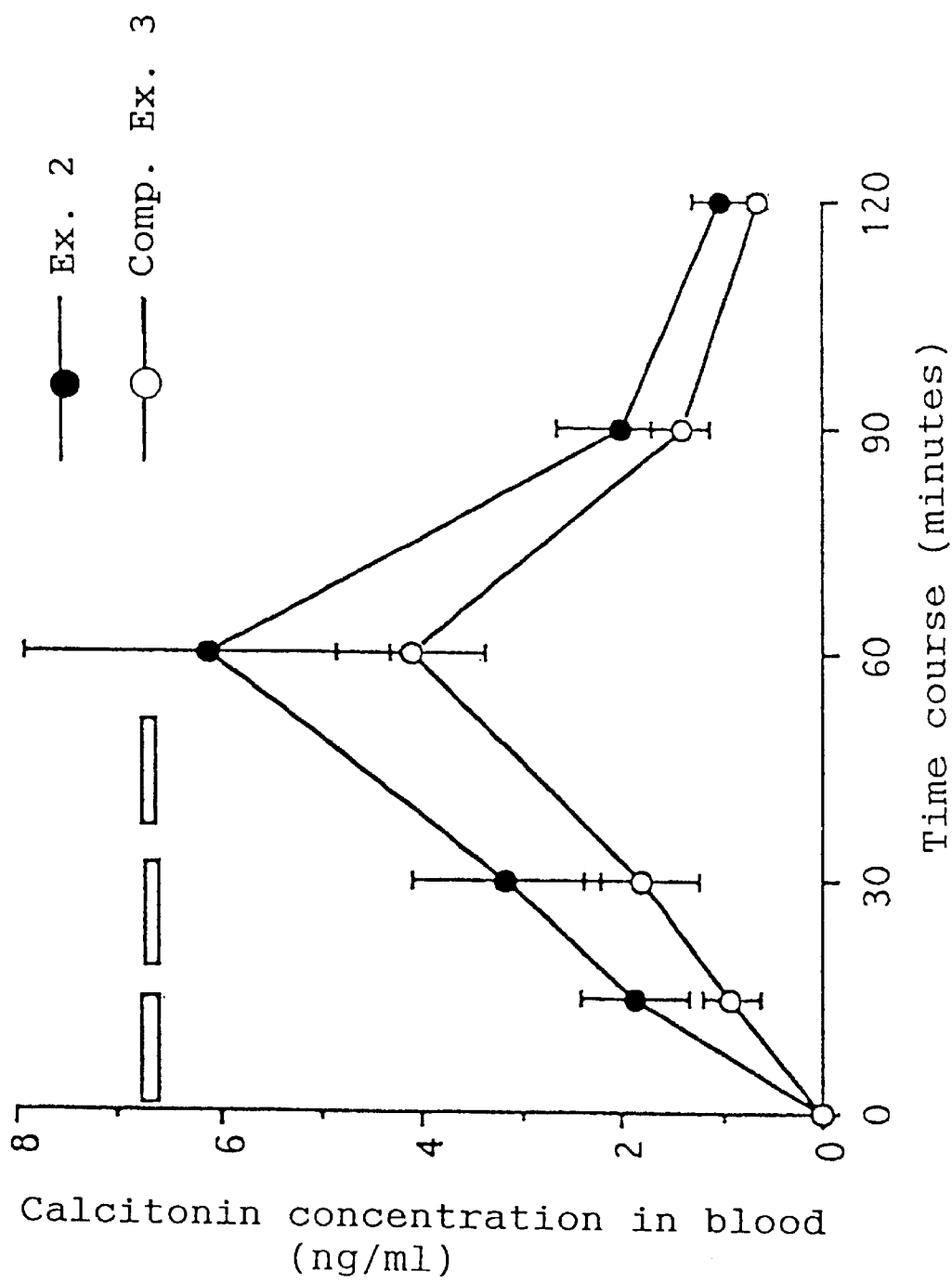
FIG. 4 is a graph showing the results in Example 2 and Comparative Example 3.

The transdermal absorbability of the calcitonin was evaluated by the iontophoresis in the following manner. Namely, an abdominal skin of a SD rat (male, 7-week aged) was clipped with a hair clipper and treated with a shaver under pentobarbital-anesthetization, and was slightly rubbed with an absorbent cotton (cotton wool) containing a 70% aqueous solution of ethanol for defatting and disinfection. The interface was attached and fixed to the abdominal skin of the rat using an adhesive tape in such a manner that the drug-holding part of the interface was in contact the skin. Further, an silver chloride electrode (2.5 cm$^2$) as a reference electrode (cathode) was fixed with the use of a 10% PVA gel (containing 0.9% of NaCl, thickness 2 mm). To the interface was supplied 120 μl of distilled water from the injection port to dissolve the drug, depolarized direct pulse current (40 kHz; duty 30%; voltage 12V) was passed for 15 minutes using an electric supplying apparatus (ADIS 4030, ADVANCE Co., Ltd., Japan), and the passing was ceased for 5 minutes. This passing-ceasing cycle was repeated three times. Then blood samples were taken periodically, and the calcitonin concentration in serum was determined by a radioimmunoassay technology. The results are shown in FIG. 4. The long and narrow 3 boxes illustrated in the upper part of FIG. 4 show electricity-passing periods.

As apparent from FIG. 4, use of the interface obtained in Example 2 insures increase of the serum calcitonin concentration by means of iontophoresis, when compared with the interface obtained in Comparative Example 3.

Further, the bioavailability was calculated from the ratio of the area under the serum concentration-time curve (AUC value) of the tested group to the AUC value obtained by intravenous administration on the same dose basis [actual intravenous dose, 1.5 International Unit (0.3 μg) of calcitonin]. As a result, the interface obtained in Comparative Example 3 showed the bioavailability of 16.6%, and in contrast, the interface obtained in Example 2 exhibited a high bioavailability of 26.0%.

What is claimed is:

1. A stabilized interface for use in an iontophoresis device, wherein one side of the interface communicates with an ion exchange membrane of the device which faces an electrically conductive gel, and the other side of the interface directly contacting the skin, said stabilized interface comprising a matrix holding a mixture comprising a water-soluble protein and a drug, wherein the matrix has a porous or capillary structure.

2. A stablilized interface as claimed in claim 1, wherein the matrix is coated with an ionic surfactant.

3. A stabilized interface as claimed in claim 2, wherein the matrix has a porous or capillary structure through which the drug is permeable.

4. A stabilized interface as claimed in claim 2, wherein the matrix is a porous organic substance or a porous ceramics having a porous or capillary structure.

5. A stabilized interface as claimed in claim 2, wherein the matrix is in the form of a sheet.

6. A stabilized interface as claimed in claim 2, wherein the ionic surfactant is a cationic surfactant.

7. A stabilized interface as claimed in claim 2, wherein the ionic surfactant is a quaternary ammonium salt.

8. A stabilized interface as claimed in claim 2, wherein the ionic surfactant is an alkylbenzyldimethylammonium halide shown by the following formula

wherein R represents an alkyl group and X represents a halogen atom.

9. A stabilized interface as claimed in claim 2, wherein the matrix is coated with the ionic surfactant in an amount of 0.1 to 50 μg per square centimeter of the matrix.

10. A stabilized interface as claimed in claim 2, wherein the matrix is coated with the ionic surfactant in an amount of 0.1 to 30 μg per square centimeter of the matrix.

11. A stabilized interface as claimed in claim 1, wherein the mixture is a homogeneous mixture comprising the water-soluble protein and the drug.

12. A stabilized interface as claimed in claim 2, wherein the protein is soluble in a proportion of not less than 5 g in 100 ml of water at 20° C.

13. A stabilized interface as claimed in claim 2, wherein the protein is at least one member selected from the group consisting of an albumin, a gelatin, a protein treated with an alkali or an acylated protein, and an enzyme-modified protein.

14. A stabilized interface as claimed in claim 2, wherein the protein is a serum albumin or gelatin.

15. A stabilized interface as claimed in claim 2, wherein the protein is a serum albumin.

16. A stabilized interface as claimed in claim 2, wherein the matrix holds 0.1 to 1,500 μg of the protein per square centimeter of the matrix.

17. A stabilized interface as claimed in claim 2, wherein the matrix holds the protein in a proportion of 0.4 to 1,200 μg per square centimeter of the matrix.

18. A stabilized interface for iontophoresis as claimed in claim 2, wherein the drug is (1) a physiologically active peptide or protein, or (2) a non-peptide physiologically active compound.

19. A stabilized interface as claimed in claim 2, wherein the drug is (1) a physiologically active peptide or protein having a molecular weight of 100 to 10,000, or (2) a non-peptide physiologically active compound having a molecular weight of 100 to 1,000.

20. A stabilized interface as claimed in claim 2, wherein the drug is at least one physiologically active peptide or a derivative thereof selected from the group consisting of adrenocorticotropic hormone, insulin, secretin, oxytocin, angiotensin, β-endorphin, glucagon, vasopressin, somatostatin, gastrins, luteinizing hormone-releasing hormone, enkephalins, neurotensin, atrial natriuretic peptide, growth hormone, bradykinin, substance P, dynorphin, thyroid-stimulating hormone, thyroid-stimulating hormone-releasing hormone, prolactin, interferons, interleukins, G-CSF, glutathione peroxidase, superoxide dismutase, desmopressin, somatomedin, endothelin, calcitonis and salts thereof.

21. A stabilized interface as claimed in claim 2, wherein the drug is a calcitonin, its derivative or a salt thereof.

22. A stabilized interface as claimed in claim 2, wherein the matrix holds 0.1 to 100 μg/cm² of the drug relative to 1 cm² of the matrix.

23. A stabilized interface for use in an iontophoresis device, wherein one side of the interface communicates with an ion exchange membrane of the device which faces an electrically conductive gel, and the other side of the interface directly contacts the skin, said stabilized interface comprising an electrically nonconductive porous matrix in the form of a sheet coated with an alkylbenzyldimethylammonium halide and holding a mixture comprising a serum albumin and a physiologically active peptide or protein.

24. A stabilized interface as claimed in claim 23, wherein the coating amount of the alkylbenzyldimethylammonium halide is 0.12 to 12 μg, the content of the serum albumin is 0.4 to 1,200 μg and the content of said physiologically active peptide or protein is 0.5 to 50 μg, respectively relative to 1 cm² of the matrix.

25. A method for stabilizing a drug in an interface for use in an iontophoresis device, wherein one side of the interface communicates with an ion exchange membrane of the device which faces an electrically conductive gel, and the other side of the interface directly contacts the skin, which comprises allowing a matrix to hold or support a mixture comprising a water-soluble protein and a drug, wherein the matrix has a porous, or capillary structure.

26. The method as claimed in claim 25, wherein the matrix is coated with an ionic surfactant.

27. A method of producing a stabilized interface according to claim 1, which comprises allowing a matrix having a porous or capillary structure to hold or support a mixture comprising a water-soluble protein and a drug.

28. A method of producing a stabilized interface according to claim 1, which comprises the steps of:
coating a matrix with an ionic surfactant, and
allowing the coated matrix to hold or support a mixture comprising a water-soluble protein and a drug, wherein the matrix has a porous or capillary structure.

29. The method according to claim 28, wherein the drug is held or supported in or on the matrix together with the water-soluble protein.

30. An applicator which comprises an electrode applicable with a direct voltage, and an interface conductible to the electrode, capable of contacting a skin and feedable with a liquid for dissolution of a drug, wherein the interface is as claimed in claim 1 or 2.

31. A method for administering a drug transdermally to a mammal using an iontophoresis device provided with an interface according to claim 1 or 2, which comprises applying an effective amount of a direct voltage to the interface according to claim 1 or 2 wherein one side of the interface directly contacts the skin of the mammal, to thereby administer said drug transdermally to the mammal.

* * * * *